(12) United States Patent
Zoabi et al.

(10) Patent No.: US 11,986,252 B2
(45) Date of Patent: May 21, 2024

(54) ENT IMAGE REGISTRATION

(71) Applicant: Biosense Webster (Israel) Ltd., Yokneam (IL)

(72) Inventors: Akram Zoabi, Kfar Masser (IL); Yoav Pinsky, Bet Keshet (IL); Itamar Bustan, Zichron Ya'acov (IL); Assaf Govari, Haifa (IL); Moshe Israel Shilemay, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 822 days.

(21) Appl. No.: 15/674,380

(22) Filed: Aug. 10, 2017

(65) Prior Publication Data
US 2019/0046272 A1 Feb. 14, 2019

(51) Int. Cl.
*A61B 34/20* (2016.01)
*G06T 7/73* (2017.01)
(Continued)

(52) U.S. Cl.
CPC ............... *A61B 34/20* (2016.02); *G06T 7/73* (2017.01); *A61B 17/24* (2013.01);
(Continued)

(58) Field of Classification Search
CPC . A61B 34/20; A61B 17/24; A61B 2090/3762; A61B 2034/2051;
(Continued)

(56) References Cited

U.S. PATENT DOCUMENTS 6,096,050 A 8/2000 Audette
9,460,512 B2 * 10/2016 Ohishi ..................... G06T 7/73
(Continued)

FOREIGN PATENT DOCUMENTS

CN 103251457 8/2013
JP 2001-500651 A 1/2001
(Continued)

OTHER PUBLICATIONS

European Search Report dated Jan. 17, 2018 from corresponding European Patent Application No. 17190097.0.
(Continued)

*Primary Examiner* — Ashley K Buran
*Assistant Examiner* — Aminah Asghar
(74) *Attorney, Agent, or Firm* — Frost Brown Todd LLP

(57) ABSTRACT

A method, including receiving a computerized tomography (CT) image of voxels of a subject's head, and analyzing the image to identify respective locations of the subject's eyes in the image, so defining a first line segment joining the respective locations. The method includes identifying a voxel subset overlaying bony sections of the head, lying on a second line segment parallel to the first line segment and on a third line segment orthogonal to the first line segment. A magnetic tracking system configured to measure positions on the subject's head is activated, and a probe, operative in the system, is positioned in proximity to the bony sections to measure positions of a surface of the head overlaying the bony sections. A correspondence between the positions and the voxel subset is formed, and a registration between the CT image and the magnetic tracking system is generated in response to the correspondence.

16 Claims, 9 Drawing Sheets

(51) Int. Cl.
*A61B 17/24* (2006.01)
*A61B 90/00* (2016.01)
(52) U.S. Cl.
CPC ............. *A61B 2034/2051* (2016.02); *A61B 2034/2065* (2016.02); *A61B 2090/3762* (2016.02); *G06T 2207/10081* (2013.01); *G06T 2207/30008* (2013.01); *G06T 2207/30041* (2013.01)
(58) Field of Classification Search
CPC .......... A61B 2034/2065; G06T 7/73; G06T 2207/30008; G06T 2207/10081; G06T 2207/30041
See application file for complete search history.

(56) References Cited

U.S. PATENT DOCUMENTS

| | | | | |
|---|---|---|---|---|
| 2004/0170337 | A1* | 9/2004 | Simon | G06T 11/00 |
| | | | | 382/254 |
| 2008/0008399 | A1* | 1/2008 | Marugame | G06T 17/10 |
| | | | | 382/285 |
| 2010/0145898 | A1* | 6/2010 | Malfliet | G06T 7/0012 |
| | | | | 706/47 |
| 2011/0295099 | A1* | 12/2011 | Bibian | A61B 5/4094 |
| | | | | 600/383 |
| 2013/0113798 | A1* | 5/2013 | Nahum | G16H 20/40 |
| | | | | 345/420 |
| 2015/0324951 | A1* | 11/2015 | Coon | G06T 17/00 |
| | | | | 345/420 |
| 2015/0342560 | A1* | 12/2015 | Davey | A61B 8/5215 |
| | | | | 600/443 |
| 2015/0351860 | A1* | 12/2015 | Piron | A61B 5/055 |
| | | | | 600/417 |
| 2016/0000518 | A1* | 1/2016 | Thoranaghatte | G06F 3/017 |
| | | | | 703/11 |
| 2016/0371539 | A1* | 12/2016 | Ming | G06K 9/00302 |
| 2017/0119481 | A1* | 5/2017 | Romo | A61B 1/307 |
| 2017/0287194 | A1* | 10/2017 | Katz | G06F 3/012 |
| 2019/0336097 | A1* | 11/2019 | Bregman-Amitai | G06K 9/627 |

FOREIGN PATENT DOCUMENTS

| | | |
|---|---|---|
| JP | 2007-130240 A | 5/2007 |
| WO | WO2016/007595 | 1/2016 |

OTHER PUBLICATIONS

Kostis Kaggelides, et al., "Locating the Eyes in CT Brain Scan Data", Master's thesis, Department of Artificial Intelligence, Edinburgh University, 1992, pp. 1-14.

European Communication dated Mar. 13, 2019, for Application No. 17190097.0, 4 pages.

Japanese Notification of Reasons for Refusal dated Jun. 15, 2021, for Application No. 2017-171815, 7 pages.

* cited by examiner

ENT IMAGE REGISTRATION

CROSS-REFERENCE TO RELATED APPLICATION

This application claims the benefit of U.S. Provisional Patent Application 62/384,823, filed Sep. 8, 2016, which is incorporated herein by reference.

FIELD OF THE INVENTION

This invention relates generally to registration of images, and specifically to images generated with different modalities that may be used for image-guided surgery.

BACKGROUND OF THE INVENTION

In image-guided surgery (IGS) a medical practitioner uses instruments that are tracked in real time so that positions and/or orientations of the instruments may be presented on images of a patient's anatomy during a surgical procedure. In some cases both the tracking and the imaging of the patient's anatomy may be implemented by one modality, such as fluoroscopy. However, because fluoroscopy uses ionizing radiation, its use should be minimized. Consequently in many scenarios an image of the patient is prepared in one modality, such as magnetic resonance imaging (MRI) or computerized tomography (CT) fluoroscopy, and the instrument tracking uses a different modality, such as electromagnetic tracking.

In order for the tracking to be effective, frames of reference of the two modalities have to be registered with each other. In the case of ear, nose, and throat (ENT) surgery, especially in the region of the sinuses, accurate registration is critical because of the proximity of the sinuses to the brain and other organs such as the optic nerves.

SUMMARY OF THE INVENTION

An embodiment of the present invention provides a method, including:
  receiving a computerized tomography (CT) image including voxels of a head of a subject;
  analyzing the image to identify respective locations of a left eye and a right eye of the subject in the image, so as to define a first line segment joining the respective locations;
  identifying a voxel subset, including voxels, overlaying bony sections of the head, lying on a second line segment parallel to the first line segment and on a third line segment orthogonal to the first line segment;
  activating a magnetic tracking system configured to measure positions on the head of the subject;
  positioning a probe, operative in the magnetic tracking system, in proximity to the bony sections to measure magnetic-system-positions of a surface of the head overlaying the bony sections;
  forming a correspondence between the magnetic-system-positions and the voxel subset; and
  generating a registration between the CT image and the magnetic tracking system in response to the correspondence.

Typically the second line segment is a preset distance above the first line segment. In a disclosed embodiment the preset distance is 5 cm.

In a disclosed embodiment the bony sections of the head are identified as voxels having Hounsfield unit values greater than or equal to +200.

In a further disclosed embodiment the third line segment overlays a nose tip of the subject.

In a yet further disclosed embodiment the second line segment and the third line segment form an upper-case T, and the method further includes displaying the CT image and positioning the upper-case T on the displayed CT image prior to positioning the probe to measure the magnetic-system-positions of the surface.

There is further provided, according to an embodiment of the present invention a method, including:
  receiving a computerized tomography (CT) image including voxels of a head of a subject;
  analyzing the image to identify respective locations of a left eye and a right eye of the subject in the image, so as to define a first line segment joining the respective locations and a second line segment orthogonally cutting the first line segment, the two line segments dividing the image into regions;
  activating a magnetic tracking system configured to measure positions on the head of the subject;
  positioning a probe, operative in the magnetic tracking system, in proximity to a surface of the head corresponding to the regions, so as to measure magnetic-system-positions of the surface;
  when a count of the magnetic-system-positions of a given region exceeds a preset threshold for the given region, providing an indication thereof and forming a correspondence between the magnetic-system-positions and the voxels of the image; and
  generating a registration between the CT image and the magnetic tracking system in response to the correspondence.

In an alternative embodiment providing the indication includes altering a visual characteristic of a sketch of the head.

In a further alternative embodiment the regions include four quadrants having respective preset thresholds.

In a yet further alternative embodiment the method includes, prior to determining the count, performing a preliminary registration between the CT image and the magnetic tracking system using magnetic-system-positions of the surface corresponding to landmark points in the CT image. The landmark points may typically include at least two of a first point below a nose tip of the subject, a second point between the eyes of the subject, a third point on a left side of the first line segment and a fourth point on a right side of the first line segment.

There is further provided, according to an embodiment of the present invention, apparatus, including:
  a magnetic sensor;
  a magnetic tracking system configured to measure locations of the magnetic sensor;
  a probe including the magnetic sensor that is configured to measure magnetic-system-positions of the probe in the system; and
  a processor, configured to:
  receive a computerized tomography (CT) image having voxels of a head of a subject;
  analyze the image to identify respective locations of a left eye and a right eye of the subject in the image, so as to define a first line segment joining the respective locations;
  identify a voxel subset, of voxels, overlaying bony sections of the head, lying on a second line segment parallel to the first line segment and on a third line segment orthogonal to the first line segment;

activate the magnetic tracking system;

receive magnetic-system-positions from the probe of a surface of the head overlaying the bony sections;

form a correspondence between the magnetic-system-positions from the probe and the voxel subset; and generate a registration between the CT image and the magnetic tracking system in response to the correspondence.

There is further provided, according to an embodiment of the present invention, apparatus, including:

a magnetic sensor;

a magnetic tracking system configured to measure locations of the magnetic sensor;

a probe including the magnetic sensor that is configured to measure magnetic-system-positions of the probe in the system; and a processor, configured to:

receive a computerized tomography (CT) image including voxels of a head of a subject;

analyze the image to identify respective locations of a left eye and a right eye of the subject in the image, so as to define a first line segment joining the respective locations and a second line segment orthogonally cutting the first line segment, the two line segments dividing the image into regions;

activate the magnetic tracking system;

receive magnetic-system-positions from the probe of a surface of the head;

when a count of the magnetic-system-positions of a given region exceeds a preset threshold for the given region, provide an indication thereof and form a correspondence between the magnetic-system-positions and the voxels of the image; and generate a registration between the CT image and the magnetic tracking system in response to the correspondence.

The present disclosure will be more fully understood from the following detailed description of the embodiments thereof, taken together with the drawings, in which:

DETAILED DESCRIPTION OF EMBODIMENTS

Overview

Figure 1:
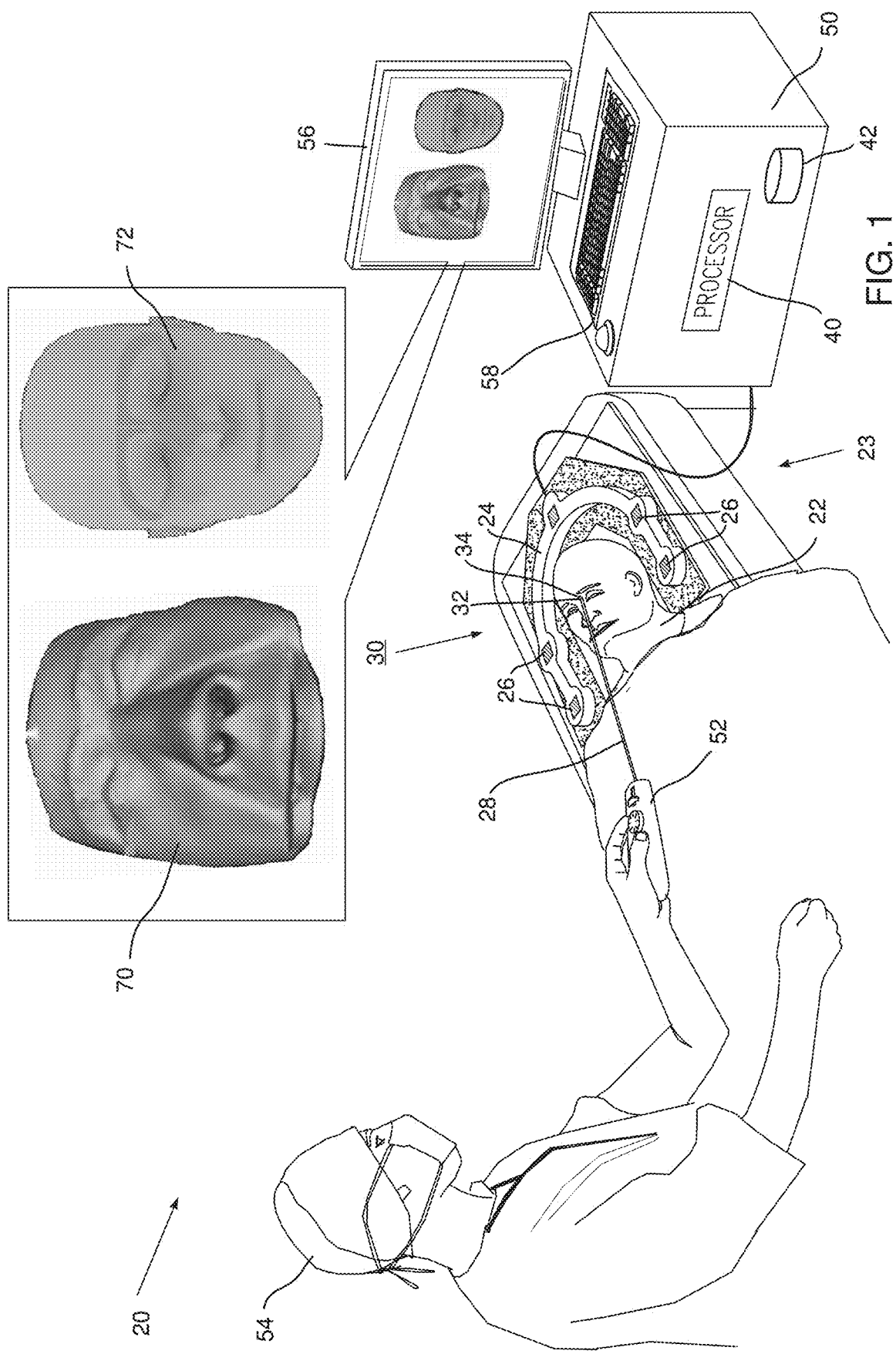
FIG. 1 is a schematic diagram illustrating an ENT (ear, nose, and throat) registration system, according to an embodiment of the present invention.

In a typical registration procedure between a CT image and a magnetic tracking system the locations of a number of different points, accessible to both systems, are acquired in both systems. As one example, the nose tip may be identified in the CT image, and the location of the nose tip may also be acquired in the magnetic tracking system. Once pairs of such points have been acquired, a theorem such as the iterative closest point (ICP) theorem, or a variation of the ICP theorem, uses a cost function to estimate the transformation, of rotation and/or translation, that best aligns, i.e., registers, the two sets of points. Typically, the process is iterated, for example by increasing the numbers of pairs of points, to improve the accuracy of the transformation.

Because of the characteristics of the CT image, the locations of external features of a patient undergoing an ENT procedure, i.e., the locations of different skin regions such as the nose tip or the earlobes, are well defined. However, in a magnetic tracking system, where a magnetic sensor is positioned on the region, the location may be poorly defined. For example, an earlobe may move when the magnetic sensor is positioned on it. For accurate registration between the two systems, it is important that regions, accessible to the magnetic system and having a low probability of movement when their location is acquired in the system, are used. Embodiments of the present invention provide methods that assist an operator to identify and use such regions.

In one embodiment the CT image of a subject is analyzed to identify respective locations of a left eye and a right eye of the subject in the image, so as to define a first line segment joining the respective locations. A voxel subset of the image is identified, the subset comprising voxels that overlay bony sections of the subject's head, and that lie on a second line segment parallel to the first line segment and on a third line segment orthogonal to the first line segment.

A magnetic tracking system that is configured to measure positions on the subject's head is activated. A probe, operative in the magnetic tracking system, is positioned in proximity to the bony sections so as to measure magnetic-system-positions of a surface of the head overlaying the bony sections.

A processor forms a correspondence between the magnetic-system-positions and the voxel subset and generates a registration between the CT image and the magnetic tracking system in response to the correspondence.

In an alternative embodiment the CT image of the subject is analyzed to identify respective locations of a left eye and a right eye of the subject in the image, so as to define a first line segment joining the respective locations and a second line segment orthogonally cutting the first line segment, the two line segments dividing the image into regions.

A magnetic tracking system that is configured to measure positions on the subject's head is activated. A probe, operative in the magnetic tracking system, is positioned in proximity to a surface of the head corresponding to the regions, so as to measure magnetic-system-positions of the surface.

A processor counts a number of the magnetic-system-positions measured, and when the count of the magnetic-system-positions of a given region exceeds a preset threshold for the given region, provides an indication thereof and forms a correspondence between the magnetic-system-positions and the voxels of the image. The processor generates a registration between the CT image and the magnetic tracking system in response to the correspondence.

DETAILED DESCRIPTION

Reference is now made to FIG. 1, which is a schematic illustration of an ENT (ear, nose, and throat) image registration system 20, according to an embodiment of the present invention. In the following description registration system 20 is assumed to be used prior to performance of a nasal sinus procedure on a patient 22. System 20 registers frames of reference of a CT (computerized tomography) image of patient 22, herein assumed by way of example to comprise a fluoroscopic CT image, and of a magnetic tracking system 23 used to track a magnetic sensor in proximity to the patient.

In system 20, and during the subsequent sinus procedure, a magnetic radiator assembly 24, comprised in the magnetic tracking system, is positioned beneath the patient's head. Assembly 24 comprises magnetic field radiators 26 which are fixed in position and which transmit alternating sinusoidal magnetic fields into a region 30 wherein the head of patient 22 is located. By way of example, radiators 26 of assembly 24 are arranged in an approximately horseshoe shape around the head of patient 22. However, alternate configurations for the radiators of assembly 24 will be apparent to those having ordinary skill in the art, and all such configurations are assumed to be comprised within the scope of the present invention.

Prior to the procedure, for the registration performed by system 20, a distal end 34 of a probe 28, having a magnetic sensor 32 at the distal end, is touched at different regions of the skin of patient 22. The signals induced in the sensor in response to its interaction with the magnetic fields enable the position of distal end 34 to be tracked, once assembly 24 has been calibrated. A probe controller 52, held by a physician 54 operating system 20, is connected to the proximal end of probe 28, the controller allowing the physician to control acquisition of the signals from sensor 32. The Carto® system produced by Biosense Webster, of Diamond Bar, CA, uses a system similar to that described herein for finding the location and orientation of a coil in a region irradiated by magnetic fields.

Elements of system 20, including radiators 26, are controlled by a system processor 40, comprising a processing unit communicating with one or more memories. Processor 40 may be mounted in a console 50, which comprises operating controls 58 that typically include a keypad and/or a pointing device such as a mouse or trackball. Console 50 connects to the radiators via a cable and/or wirelessly, and also connects to other elements of system 20, such as controller 52 of probe 28. Physician 54 uses controller 52 and operating controls 58 to interact with the processor while performing the registration of system 20. During the registration process, a surface image 70 and a face sketch 72, for viewing by the physician, are presented on a screen 56. The functions of surface image 70 and face sketch 72 are described in detail below. (Subsequent to the registration process, physician 54 uses the operating controls to interact with the processor while performing the procedure, and the processor may present results of the procedure on screen 56.)

Processor 40 uses software stored in a memory 42 to operate system 20. The software may be downloaded to processor 40 in electronic form, over a network, for example, or it may, alternatively or additionally, be provided and/or stored on non-transitory tangible media, such as magnetic, optical, or electronic memory.

Processor 40 uses the software, inter alia, to operate magnetic radiators 26 of assembly 24. As stated above the radiators transmit sinusoidal alternating magnetic fields of different frequencies into region 30, including the head of patient 22, and the fields from the radiators induce signals in sensor 32. The processor analyzes the signals to derive location and orientation values, measured with respect to a frame of reference defined by the assembly, for the sensor and thus for the distal end of probe 28.

Prior to performance of the procedure a CT image of patient 22 is acquired for use by system 20. Data of the CT image is stored in memory 42 for subsequent retrieval by processor 40. As is described below, the processor uses the stored data to present surface image 70 on screen 56.

Figure 2:
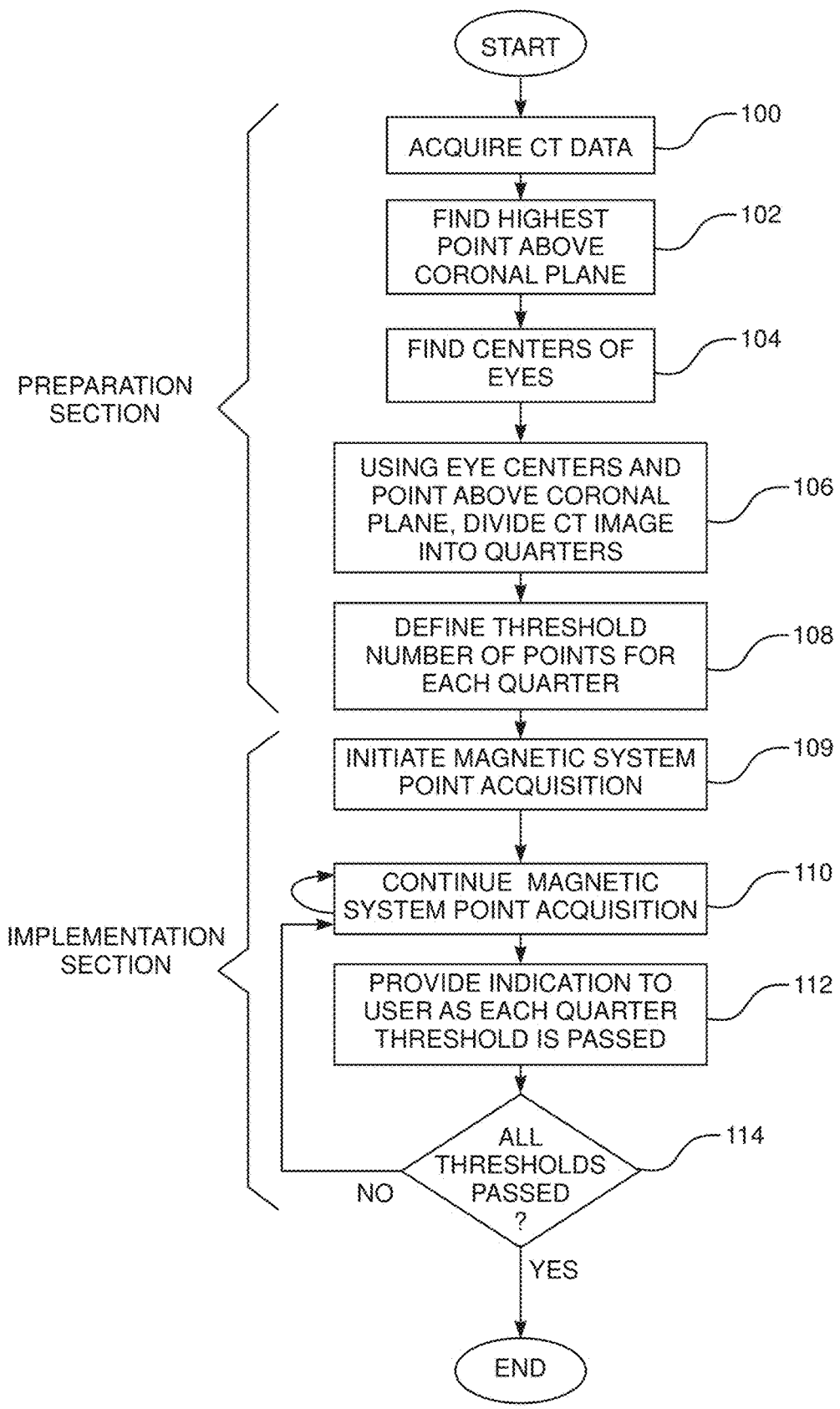
FIG. 2 is a flowchart of steps of a process for the system of FIG. 1, according to an embodiment of the present invention.
Figure 3:
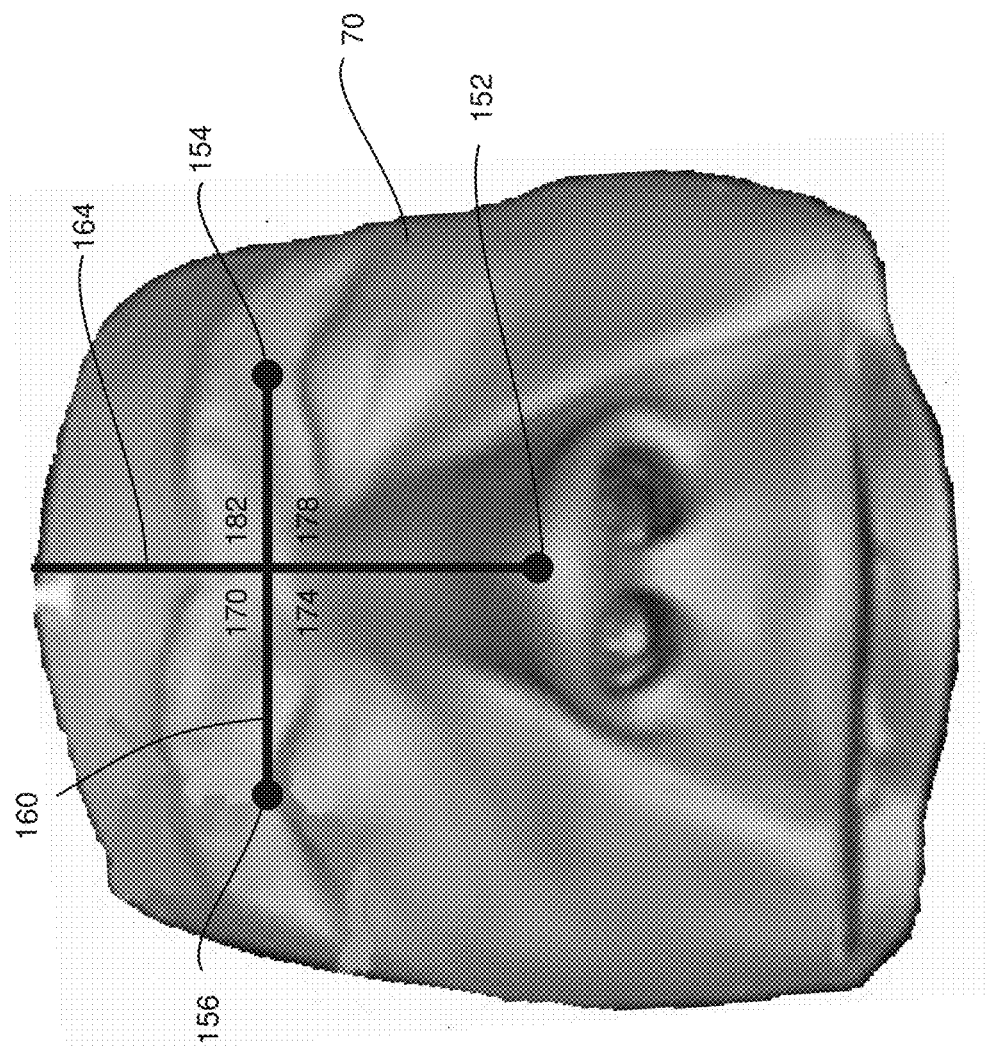
FIGS. 3-5 are schematic diagrams illustrating the steps of the flowchart of FIG. 2, according to an embodiment of the present invention.

FIG. 2 is a flowchart of steps of a process implemented in system 20, and FIG. 3 is a schematic figure illustrating first steps of the flowchart, according to an embodiment of the present invention. The flowchart is divided into two sections: a first preparation section comprising steps 100-108, and a subsequent implementation section comprising steps 109-114. The implementation section of the flowchart may be performed days, or even weeks, after completion of the preparation section.

In an initial step 100 a CT image of the head of patient 22 is generated, and the acquired data of the image is stored in memory 42.

In a first image analysis step 102 processor 40 accesses the stored CT data and generates surface image 70 of the head of the patient. The processor then finds a highest point 152 of the surface image that is above the coronal plane of the patient. Typically the highest point corresponds to the nose tip of the patient.

In a second image analysis step 104 the processor 40 finds centers 154, 156 of the eyes of the patient. An article "Locating the eyes in CT brain scan data" in the Proceedings of the 6th international conference on Industrial and Engineering Applications of Artificial Intelligence and Expert Systems, pgs. 507-517, published in 1993, describes one method for finding the centers of the eyes, and the article is incorporated herein by reference. Other methods for finding the centers will be apparent to those having ordinary skill in the art, and all such methods are assumed to be comprised within the scope of the present invention. A description of a method for finding centers of the eyes of a patient, in an image of the patient, is provided in the Appendix below.

In a construction step 106 the processor constructs a line 160 joining the two eye centers, found in step 104. In addition, the processor constructs a line 164 orthogonal to line 160, parallel to the coronal plane, and passing through a projection of the highest point found in step 102. As illustrated in FIG. 3, the two lines divide the corresponding surface image into four quarter regions 170, 174, 178, 182, also herein termed quadrants.

In a threshold definition step 108, processor 40 stores minimum numbers of points to be acquired in each of quadrants 170, 174, 178, 182. In one embodiment the minimum numbers are respectively 20, 12, 12, and 20. However, the minimum numbers may be smaller or larger than these values, and may be the same or different for all sections. The inventors have found the values for the number of points stated above give satisfactory results, and those with ordinary skill in the art will be able to determine other sets of values, that give satisfactory results, without undue experimentation.

Step 108 completes the preparation section of the flowchart.

In an initial magnetic system point acquisition step 109, which is the beginning of the implementation section of the flowchart, physician 54 activates probe 28 so that signals from magnetic sensor 32 (at the probe's distal end) may be acquired by processor 40. Typically, signals are acquired when the physician has positioned distal end of the probe on a desired portion of the patient's skin, and at the same time activates system 20, for example using a control in controller 52 of the probe, to save the acquired signals to memory 42.

In step 109 the physician positions the distal end at a preset number of "landmark" points on the patient's skin. The landmark points correspond to predetermined CT positions in the CT image that processor 40 is able to identify. In one embodiment four landmark points, comprising a point below the tip of the patient's nose, the left and right sides of the patient's face besides the eyes, and a point between the eyes are used, and signals from magnetic sensor 32 are acquired at these points.

Once the magnetic sensor signals have been acquired, the processor calculates respective magnetic positions in the magnetic assembly frame of reference, so generating four ordered pairs of positions, each ordered pair being a correspondence and having the form (magnetic position, CT position).

Processor 40 uses the set of ordered pairs to generate a preliminary registration, i.e., a transformation comprising a translation and/or a rotation, that aligns the CT system with the magnetic assembly.

While the embodiment described above uses four landmark points, the inventors believe that fewer than four points, possible only two points, may be sufficient to generate the preliminary registration.

Figure 4:
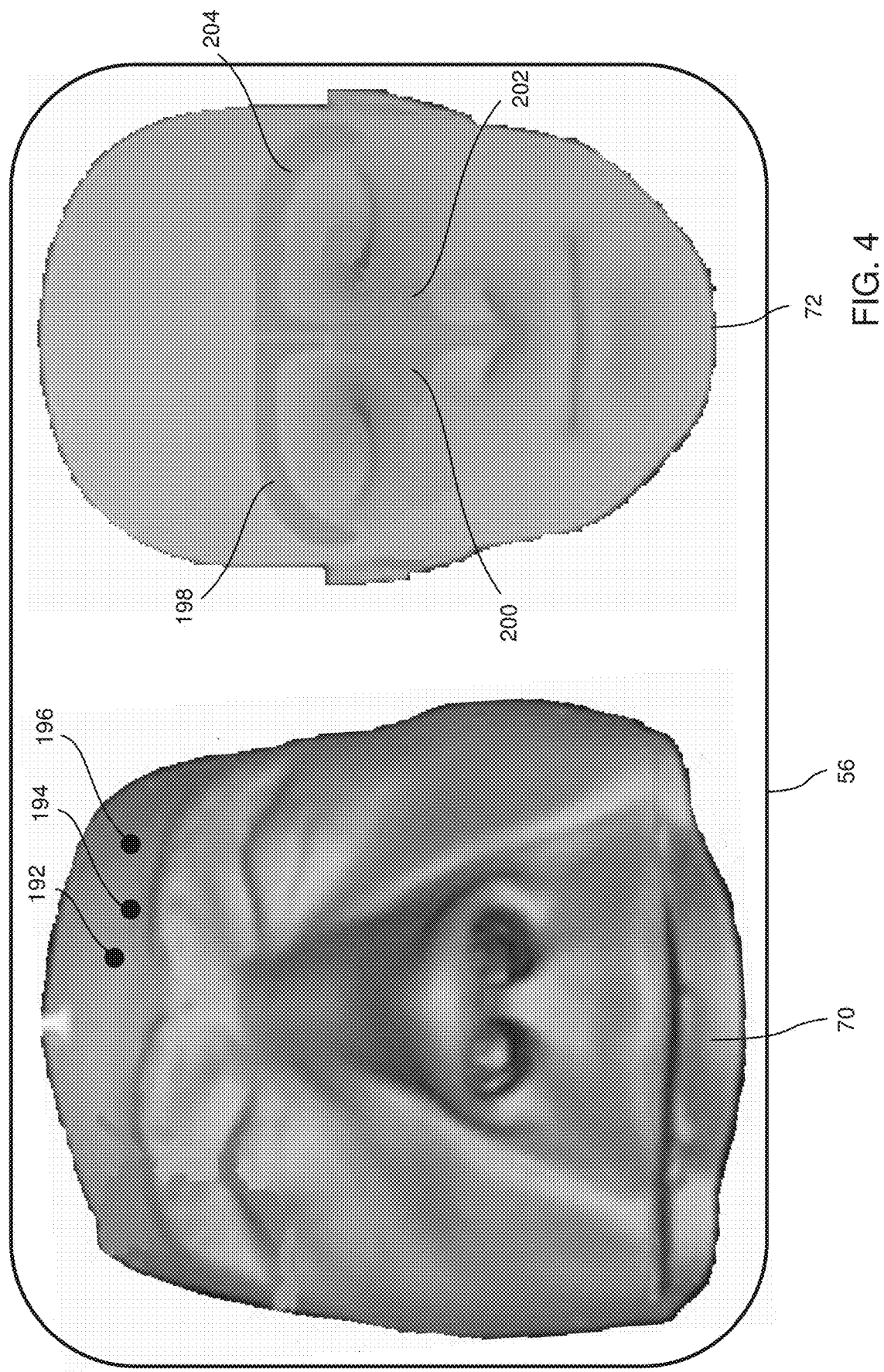
Figure 5:
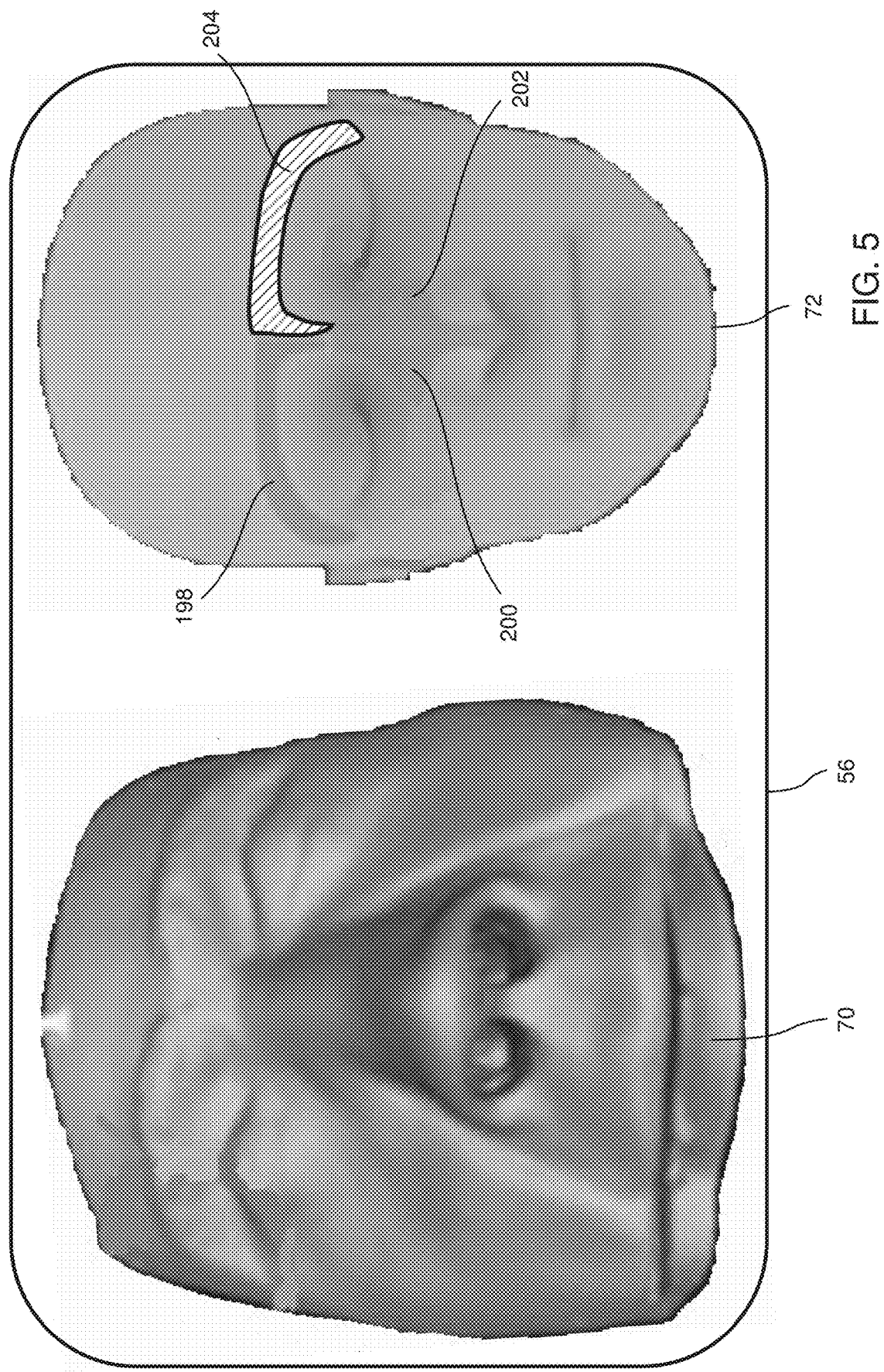

FIG. 4 illustrates an initial display of surface image 70 and face sketch 72 on screen 56, and FIG. 5 illustrates a subsequent display of the surface image and of the sketch, according to an embodiment of the present invention. As is described below, the sketch is used as a visual indicator for a user of system 20, to indicate when sufficient data has been collected for accurate registration of the frames of reference of the CT image and of the magnetic tracking system (as compared with the preliminary registration found in step 109).

Returning to the flowchart, in a continuing acquisition step 110 the processor displays the surface image and the human face sketch on screen 56, as is illustrated in FIG. 4. Physician 54 continues to acquire signals from magnetic sensor 32, and processor 40 saves the acquired signals to memory 42. In some embodiments a notice is displayed on screen 56, suggesting that the physician acquires signals when distal end 34 is positioned close to bony features of the patient, such as the bridge of the nose and the eyebrows or forehead.

Each time signals are acquired, a respective mark is placed on surface image 150, in a region corresponding approximately to the location of distal end 34 as determined by the preliminary registration of step 109. FIG. 4 illustrates, by way of example, three marks 192, 194, and 196.

Each time signals are acquired the processor uses the location determined by the signals to update the ICP theorem, using the new location as an addition to a source cloud of points. (Surface image 70 corresponds to a reference cloud of points used by the ICP theorem.)

In addition, each time signals are acquired the processor increments a counter for the quarter region where the signal is acquired.

In a continuing step 112, the processor checks the counters for each quarter region, and as a threshold of acquired locations is reached for the region, the processor provides an indication to the physician that the region threshold has been reached.

In an embodiment of the present invention the indication provided is a visual indication wherein a portion of sketch 70, that was initially gray, is altered visually, such as by being colored or shaded. FIGS. 4 and 5 illustrate four gray areas 198, 200, 202, and 204, respectively corresponding to quarter regions 170, 174, 178, 182, that are used as indication areas. FIG. 5 illustrates that area 204 has been shaded, indicating that the threshold for quarter region 182 has been reached.

In a condition step 114 the physician checks, by inspection of the sketch, if the thresholds of all quarter regions have been reached. If the check returns positive, the physician may stop acquiring locations with probe 28. If the check returns negative, i.e., if one or more visual indications of reaching a threshold are not provided, the flowchart returns to step 110 and the physician continues acquiring points with probe 28.

The inventors have found that implementation of system 20, as described above, provides a fast, efficient, and accurate registration of the magnetic system frame of reference with the CT imaging frame of reference.

Figure 6:
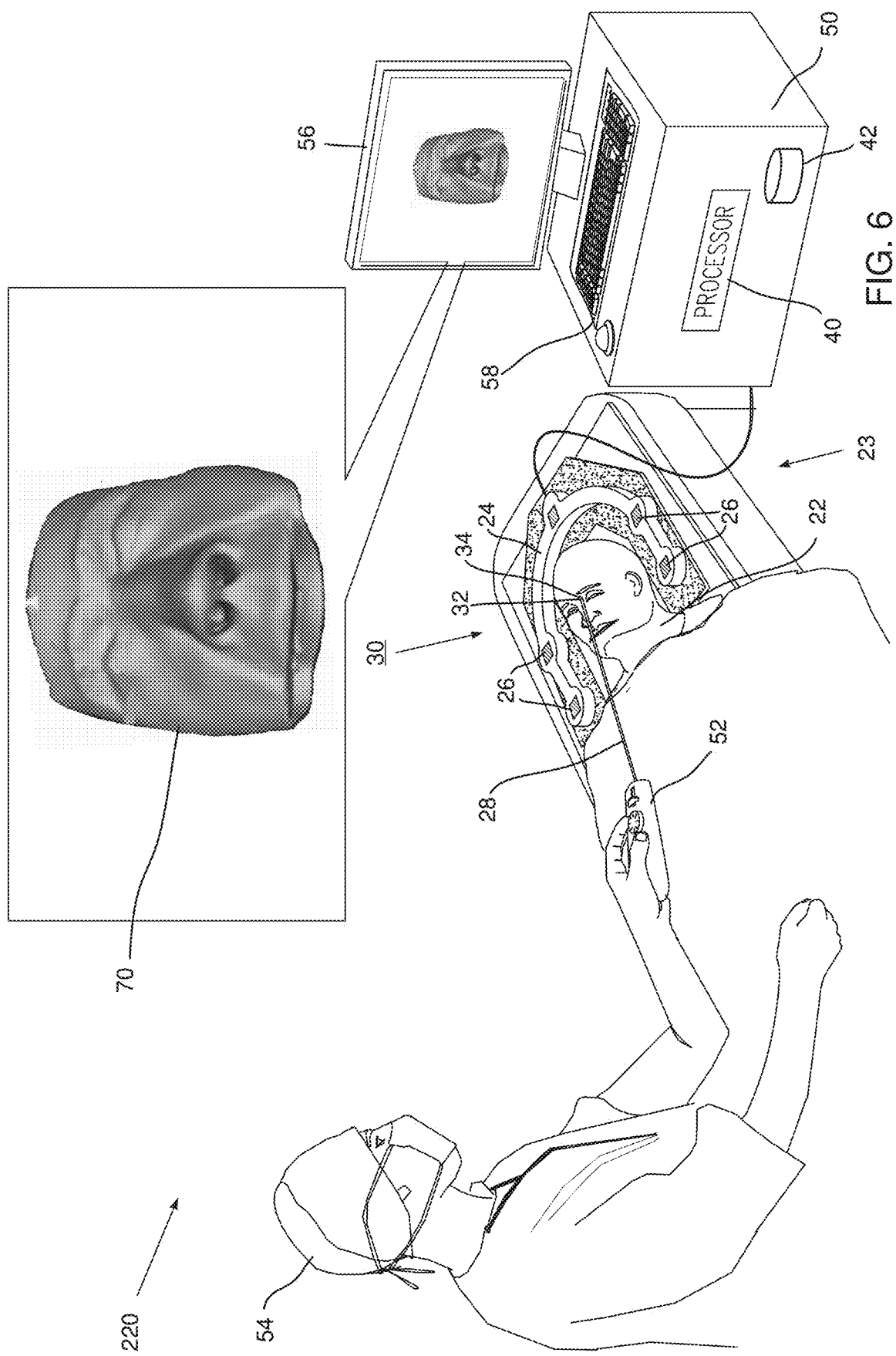
FIG. 6 is a schematic diagram illustrating an alternative ENT registration system, according to an embodiment of the present invention.

Reference is now made to FIG. 6, which is a schematic illustration of an alternative ENT image registration system 220, according to an embodiment of the present invention. Apart from the differences described below, the operation of system 220 is generally similar to that of system 20 (FIGS. 1-5), and elements indicated by the same reference numerals in both systems 20 and 220 are generally similar in construction and in operation.

In contrast to system 20, in system 220 no visual indicator such as sketch 72 is presented on screen 56, so that the display on the screen may be only surface image 70. Also in contrast to the steps of the flowchart of FIG. 2 used by system 20 to register the two frames of reference, system 220 uses steps of a different flowchart, as described hereinbelow.

Figure 7:
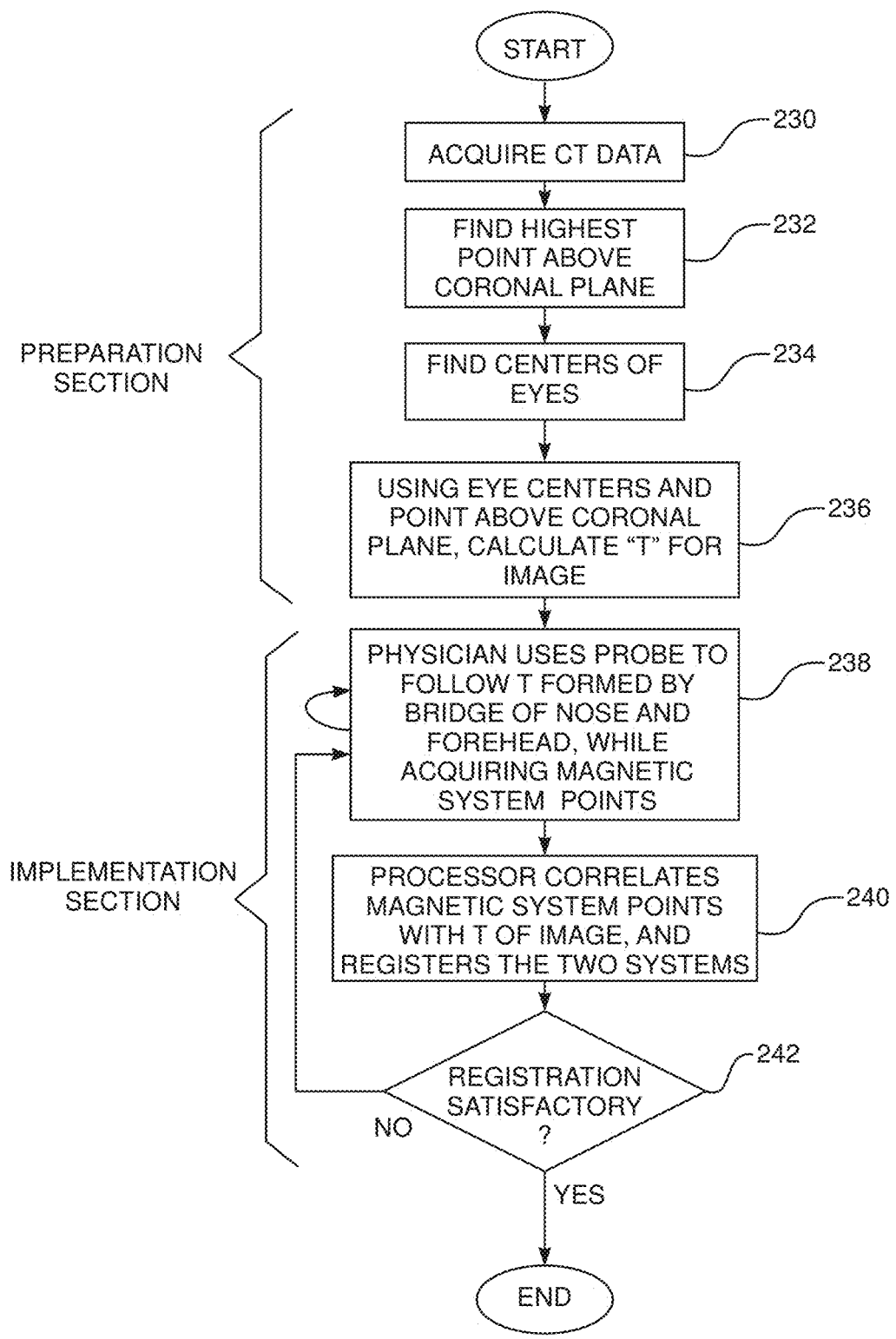
FIG. 7 is a flowchart of steps of an alternative process for the system of FIG. 6, according to an embodiment of the present invention.
Figure 8:
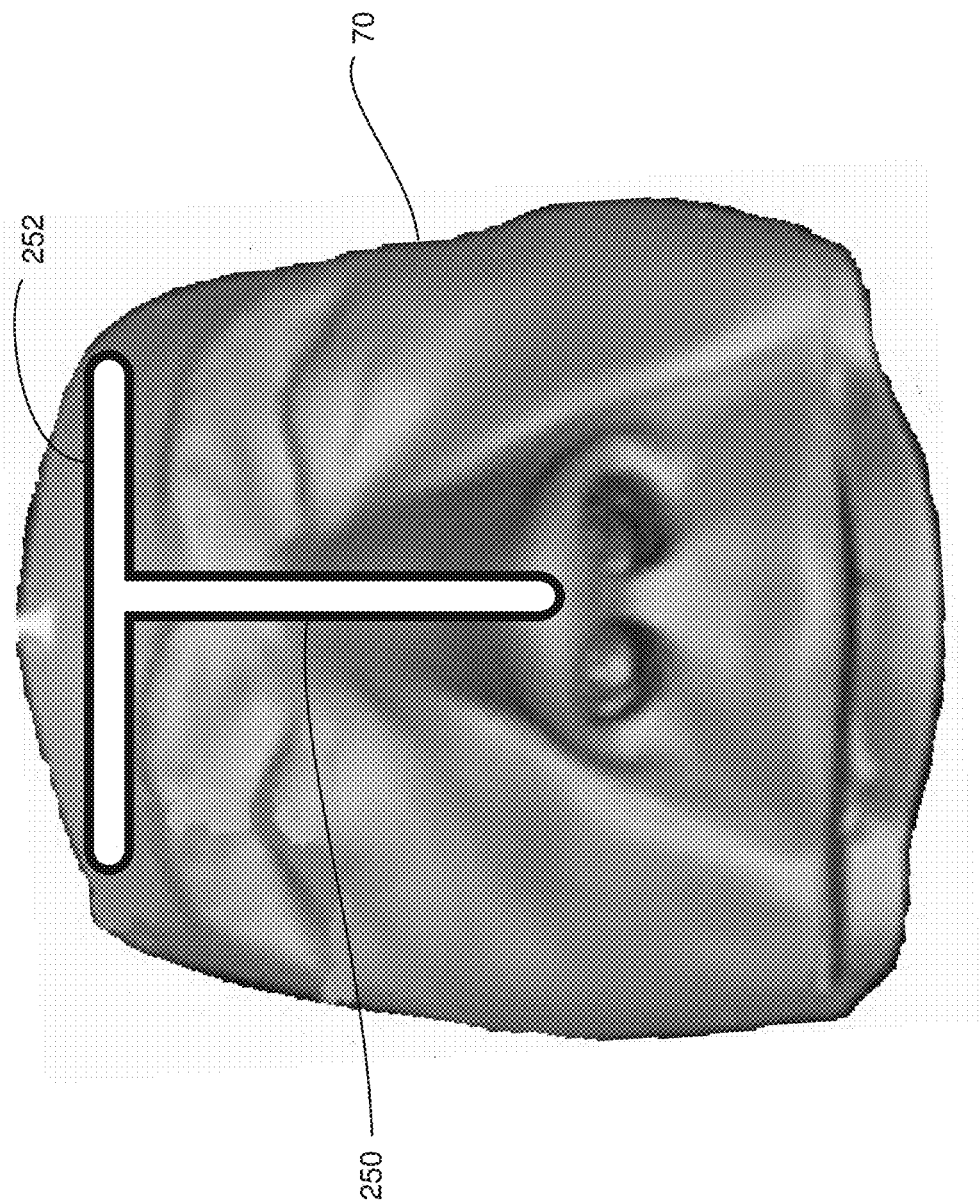
FIG. 8 is a schematic diagram illustrating a step of the flowchart of FIG. 7, according to an embodiment of the present invention.

FIG. 7 is a flowchart of steps of a process implemented in system 220, and FIG. 8 illustrates one of the steps, according to an embodiment of the present invention. As for the flowchart of FIG. 2, the flowchart of FIG. 7 has an initial preparation section followed by and implementation section. In the flowchart of FIG. 7 steps 230, 232, and 234 are substantially respectively the same as steps 100, 102, and 104 of the flowchart of FIG. 2.

In an image analysis step 236, the processor analyzes surface image 70 generated in step 232, using the values acquired in steps 232 and 234, to delineate voxels within the acquired image of an upper-case "T" shape. The T shape comprises the bridge of the patient's nose as a vertical line 250 (FIG. 8) of the T. To determine voxels of the vertical line the processor starts from the nose tip determined in step 232, and finds other voxels of the bridge of the nose, i.e., the bony section of the nose, by looking for local maxima in surface image 70 in proximity to, and vertically above, the nose tip. The processor continues this process iteratively to find voxels corresponding to the complete vertical line 250 of the T shape.

To find voxels corresponding to a horizontal line 252 of the T shape, the processor selects voxels that are a preset vertical distance above a line joining the patient's eye centers, as found in step 234. In one embodiment the preset distance is 5 cm above the eye center line, but in other embodiments the distance may be larger or smaller than 5 cm. The preset distance is chosen so that the voxels of the horizontal line overlie the bony section of the patient's forehead.

If necessary, vertical line 250 of voxels, found as described above, is extended so that it meets horizontal line 252 of voxels.

It will be understood that in analysis step 236 the processor generates a subset of the set of voxels comprising surface image 70. The subset is in the general shape of an upper-case T, and the voxels of the subset 34 overlay bony sections of the patient's head. In one embodiment the bony sections correspond to voxels of the full CT image having Hounsfield unit values greater than or equal to approximately +200. Typically, both the vertical line and the horizontal line of voxels are more than one voxel wide.

Step 236 concludes the preparation section of the flowchart.

In the implementation section of the flowchart, in an implementation step 238, physician 54 moves distal end 34 of probe 28 along the bridge of the nose of patient 22, and along the forehead of the patient. In other words, the physician moves the distal end of the probe in a "T" pattern. In some embodiments a diagram such as FIG. 8 is displayed on screen 56 so as to direct the physician to move the probe in the T pattern. During the movement the physician uses controller 52 to acquire signals from sensor 32 in the probe.

In a correlation and registration step 240, the processor uses the ICP theorem to correlate the points acquired in step 238 with the subset of voxels generated in step 236. While performing the correlation the processor also registers the two frames of reference, i.e., of the magnetic system and of the CT imaging system. The theorem uses the subset of voxels as the reference set of points, and the points acquired in step 238 as the source set of points.

In a condition step 242 the processor checks if the registration performed in step 240 is sufficiently accurate, i.e., if the errors associated with the cost function generated by the ICP theorem are sufficiently small, typically below a preset threshold. If the condition returns positive, then a notice is typically provided on screen 56 informing the physician that she/he may cease acquiring points. The notice may also suggest that the physician performs a verification of the registration, such as by touching predefined positions and having the processor mark these positions on the CT image, and/or by measuring distances between such positions. If the condition returns negative, or if the verification fails, the flowchart returns to step 238 where the physician continues to acquire points with probe 28.

The inventors have found that since the reference set of points and the source set of points have the same "T" shape, and because both sets are small subsets of their respective sets, using the ICP theorem provides extremely quick and accurate registration of the magnetic system frame of reference with the CT imaging frame of reference.

APPENDIX

Figure 9:
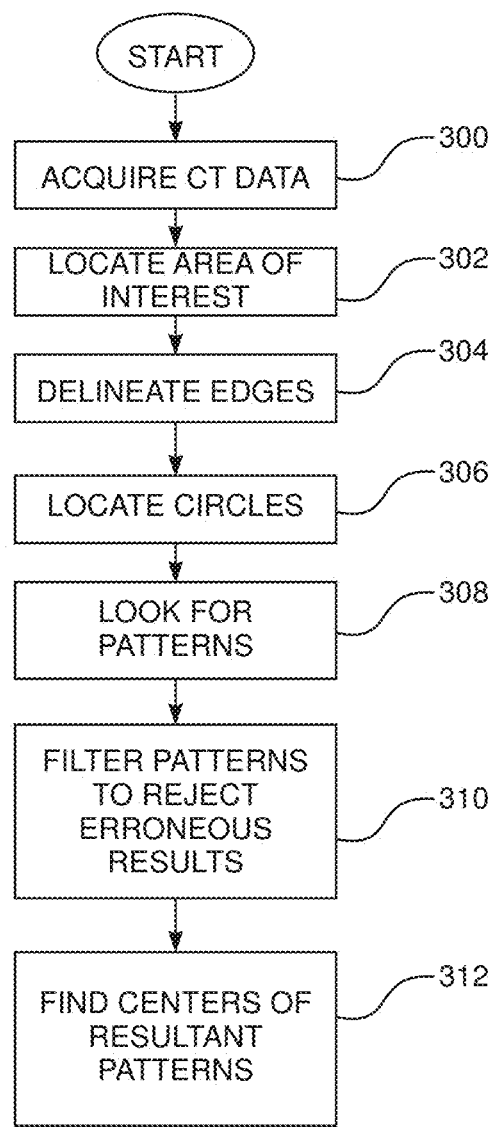
FIG. 9 is a flowchart showing steps for finding centers of the eyes of a patient in a CT image of the patient, according to an embodiment of the present invention.

FIG. 9 is a flowchart showing steps for finding centers of the eyes of a patient in a CT image of the patient, according to an embodiment of the present invention. The steps of the flowchart are based on the above-referenced article: "Locating the eyes in CT brain scan data," and in the following description the steps of the flowchart are assumed be implemented by processor 40 operating on a CT image of the head of patient 22.

An initial step 300 is substantially as step 100 described above.

In a locate area of interest step 302 processor 40 delineates a bounding box for the patient's head in the CT image, for example by raster scanning slices of the image to find the surface of the head in each slice.

In an edge detection step 304, the processor demarcates edges of entities within the bounding box, typically by using the Canny algorithm.

In a circle location step 306, the processor finds circles defined by the edges, typically by using a Hough Transform. As is known in the art, the Hough Transform uses a voting procedure to find instances of objects of a given shape, in this case circles. Typically, line voting may be used, the line being defined with respect to a circle. The results of the Hough Transform may be enhanced using the converging squares algorithm.

In a pattern recognition step 308, the circles found in step 306 are checked to see if they form a pattern, i.e., that there are corresponding circles in clusters of adjacent slices of the CT image. The ISODATA unsupervised clustering algorithm may be used to formulate clusters of circles.

In a filtration step 310, the clusters of step 308 are filtered to remove erroneous results. In one embodiment the Hough Transform may be used a second time, using known possible dimensions for an eye sphere radius.

In a final step 312 the centers of the remaining clusters after step 310 are taken as the centers of the eyes in the CT image.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:
1. A method, comprising:
 (a) receiving a computerized tomography (CT) image comprising voxels of a head of a subject;
 (b) analyzing the image to identify respective locations of a left eye and a right eye of the subject in the image, so as to define a first line segment joining the respective locations;
 (c) identifying a voxel subset from the voxels of the head of the subject, the voxel subset comprising:
  (i) voxels, overlaying a first bony section of the head, identified based on their lying on a second line segment parallel to the first line segment; and
  (ii) voxels, identified based on their overlaying a second bony section of the head, lying on a third line segment orthogonal to the first line segment;
 (d) activating a magnetic tracking system configured to measure positions on the head of the subject;
 (e) positioning a probe, operative in the magnetic tracking system, in proximity to the first and second bony sections to measure magnetic-system-positions of a surface of the head overlaying the first and second bony sections;
 (f) forming a correspondence between the magnetic-system-positions and the voxel subset; and
 (g) generating a registration between the CT image and the magnetic tracking system in response to the correspondence.

2. The method according to claim 1, wherein the second line segment is identified based on the second line segment being a preset distance above the first line segment.

3. The method according to claim 2, wherein the preset distance is 5 cm.

4. The method according to claim 1, and comprising identifying the first and second bony sections of the head as voxels having Hounsfield unit values greater than or equal to +200.

5. The method according to claim 1, wherein:
(A) the third line segment overlays a nose tip of the subject;
(B) the voxels identified based on overlaying the second bony section are identified based on:
  (i) starting from the nose tip of the subject; and
  (ii) finding local maxima in proximity to, and vertically above, the nose tip.

6. The method according to claim 1, wherein the second line segment and the third line segment form an upper-case T, the method further comprising displaying the CT image and positioning the upper-case T on the displayed CT image prior to positioning the probe to measure the magnetic-system-positions of the surface.

7. The method of claim 1, wherein generating the registration comprises applying an iterative closest point theorem on the magnetic-system-positions and the voxel subset.

8. The method of claim 1, wherein the magnetic-system-positions of the surface of the head overlaying the first and second bony sections are acquired by moving a distal end of the probe in a pattern based on the second line segment and the third line segment.

9. An apparatus, comprising:
(a) a magnetic sensor;
(b) a magnetic tracking system configured to measure locations of the magnetic sensor;
(c) a probe comprising the magnetic sensor that is configured to measure magnetic-system-positions of the probe in the system; and
(d) a processor, configured to:
  (i) receive a computerized tomography (CT) image comprising voxels of a head of a subject,
  (ii) analyze the image to identify respective locations of a left eye and a right eye of the subject in the image, so as to define a first line segment joining the respective locations,
  (iii) identify a voxel subset from the voxels of the head of the subject, the voxel subset comprising:
    (A) voxels, overlaying a first bony section of the head, identified based on their lying on a second line segment parallel to the first line segment, and
    (B) voxels, identified based on their overlaying a second bony section of the head, lying on a third line segment orthogonal to the first line segment,
  (iv) activate the magnetic tracking system,
  (v) receive magnetic-system-positions from the probe of a surface of the head overlaying the first and second bony sections,
  (vi) form a correspondence between the magnetic-system-positions from the probe and the voxel subset, and
  (vii) generate a registration between the CT image and the magnetic tracking system in response to the correspondence.

10. The apparatus according to claim 9, wherein the processor is configured to identify the second line segment based on the second line segment being a preset distance above the first line segment.

11. The apparatus according to claim 10, wherein the preset distance is 5 cm.

12. The apparatus according to claim 9, wherein the processor is configured to identify the first and second bony sections of the head as voxels having Hounsfield unit values greater than or equal to +200.

13. The apparatus according to claim 9, wherein:
(A) the third line segment overlays a nose tip of the subject;
(B) the voxels identified based on overlaying the second bony section are identified based on:
  (i) starting from the nose tip of the subject; and
  (ii) finding local maxima in proximity to, and vertically above, the nose tip.

14. The apparatus according to claim 9, wherein the second line segment and the third line segment form an upper-case T, the processor further configured to display the CT image and positioning the upper-case T on the displayed CT image prior to receiving the magnetic-system-positions of the surface from the probe.

15. The apparatus of claim 9, wherein generating the registration comprises applying an iterative closest point theorem on the magnetic-system-positions and the voxel subset.

16. The apparatus of claim 9, wherein receiving magnetic-system-positions from the probe of the surface of the head overlaying the first and second bony sections comprises receiving magnetic system positions obtained by moving the distal end of the probe in a pattern based on the second line segment and the third line segment.

* * * * *

UNITED STATES PATENT AND TRADEMARK OFFICE
CERTIFICATE OF CORRECTION

| | | |
|---|---|---|
| PATENT NO. | : 11,986,252 B2 | Page 1 of 1 |
| APPLICATION NO. | : 15/674380 | |
| DATED | : May 21, 2024 | |
| INVENTOR(S) | : Zoabi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1090 days.

Signed and Sealed this
Eighth Day of October, 2024

Katherine Kelly Vidal
*Director of the United States Patent and Trademark Office*